United States Patent [19]

Aomori

[11] Patent Number: 5,005,558
[45] Date of Patent: Apr. 9, 1991

[54] ENDOSCOPE

[75] Inventor: Kohkichi Aomori, Yokohama, Japan

[73] Assignee: Kabushiki Kaisha Toshiba, Kawasaki, Japan

[21] Appl. No.: 352,311

[22] Filed: May 16, 1989

[30] Foreign Application Priority Data

May 16, 1988 [JP] Japan .................. 63-117024
Dec. 1, 1988 [JP] Japan .................. 63-302202

[51] Int. Cl.⁵ .............................. A61B 1/00
[52] U.S. Cl. ...................................... 128/4
[58] Field of Search ................ 128/4, 6; 138/120

[56] References Cited

U.S. PATENT DOCUMENTS

| | | | |
|---|---|---|---|
| 512,558 | 1/1894 | Landis | 138/120 |
| 1,153,187 | 7/1915 | Berry | 138/120 |
| 3,190,286 | 6/1965 | Stokes | 138/120 |
| 3,266,059 | 8/1966 | Stelle | 128/4 |
| 4,700,693 | 10/1987 | Lia et al. | 128/4 |
| 4,790,294 | 12/1988 | Allred, III et al. | 128/4 |
| 4,796,607 | 1/1989 | Allred, III et al. | 128/4 |

FOREIGN PATENT DOCUMENTS

| | | | |
|---|---|---|---|
| 3830874 | 3/1989 | Fed. Rep. of Germany | 138/120 |
| 63-136014 | 6/1988 | Japan . | |
| 63-281618 | 11/1988 | Japan . | |
| 0925310 | 5/1982 | U.S.S.R. | 128/4 |

OTHER PUBLICATIONS

S. Hirose, "Moving Arm with Bending Part", Engineering of Biomechanics, Chap. 9, Sec. 3, 1987, pp. 156–165.

*Primary Examiner*—Benjamin Layno
*Attorney, Agent, or Firm*—Foley & Lardner

[57] ABSTRACT

An endoscope includes an operating body having a knob, a flexible insertion tube having a bending tube part, to be inserted into an object to be observed, and wires for bending the bending tube part by operating the knob. The bending tube part includes ring link members having a tubular form, and flexible connection members for coupling adjacent two ring link members at upper and lower or left and right sides thereof, alternately, to connect the ring link members with one another in series.

19 Claims, 3 Drawing Sheets

ENDOSCOPE

BACKGROUND OF THE INVENTION

1. Field of the Invention

The present invention relates to an endoscope, and more particularly to a bending tube part of an endoscope for observing and treating the inside or internal organs of a body or of machinery.

2. Description of the Background Art

As shown in FIG. 1, an endoscope 1 includes an operating body 2, a flexible insertion tube 3 and an electric cord 4 to be connected to an electrical plug. The flexible insertion tube 3 includes a flexible tube part 5, a bending tube part 6 connected to the end of the flexible tube part 5, and an end part 7 connected to the end of the bending tube part 6. The end part 7 is provided with treating members such as a charge coupled device (CCD) and so forth. The operating body 2 has an operating knob 8 for flexibly bending the bending tube part 6 in up and down and left and right directions.

In FIG. 2, there is shown a conventional bending tube part 6 of an endoscope 1, which comprises a plurality of ring link members 11 having a tubular form, connected with one another in series through pin members 15. In the ring link members 11, a light guide, electric leads for an image guide, the CCD and the like, tubes for feeding air and water and sucking air, a forceps channel and the like are passed. Usually, the ring link members 11 are covered by a braid and an outer cover. In each ring link member 11, a diameter of one end portion 12 is enlarged so as to fit and receive the other end of another ring link member 11. Each ring link member 11 is integrally provided with four connection projections 13 having a hole and projecting frontwards and rearwards, for instance, two connection projections 13 are connected to left and right sides of one end (e.g., normal diameter end portion) of the ring link member 11 and the other two connection projections 13 are connected to upper and lower sides of the other end (e.g., enlarged diameter end portion 12) of the ring link member 11. The two adjacent ring link members 11 are connected with one another by pivotally connecting the connection projections 13 by using pin members 15 while the normal diameter end portion of one ring link member 11 is fitted in the enlarged diameter end portion 12 of another ring link member 11, resulting in the bending tube part 6 can freely be bent in the up and down and left and right directions.

Each ring link member 11 is also formed with wire guide members 16 having a tubular ring form on the inside wall in the same longitudinal planes where the pin members 15 are aligned, and operating wires 17 are passed through the holes of the wire guide members 16. One end of each of the wires 17 is secured to the ring link member 11 positioned in the front end and the other ends of the wires 17 are connected to the knob 8 of the body 2. Hence, by pulling and slackening out the wires 17 by handling the operating knob 8, the bending tube part 6 can be bent at a desired angle in the desired direction.

However, in the bending tube part 6 of the above described conventional endoscope, the ring link members 11 and the pin members 15 are always contacted with one another with inevitable friction during the pivot motion of the ring link members 11 around the pin members 15 when the bending tube part 6 is bent by operating the knob 8. Thus, unnecessary play or clearance is increased between the ring link members 11 and the pin members 15, and, as a result, the life of the bending tube part 6 becomes short.

Further, when the inside of the internal organs of the body or a limited narrow space in the machinery is observed, the radius of the curvature of the bending tube part 6 is preferably small. However, in the conventional bending tube part, since the bending tube part 6 comprises as a whole a series of uniform joint structure, when the end part 7 connected to the bending tube part 6 is bent even in a small amount, the root portion of the bending tube part 6, i.e., the portion near the flexible tube part 5 is firstly bent. Accordingly, after the part of the bending tube part 5 is contacted with the inside wall of the object to be observed, the positioning of the end part 7 in the desired position becomes difficult. In particular, in the operation within an internal organ of a body, the inside wall of the internal organ is often damaged, and pain caused to a patient.

Further, in the conventional bending tube part 6, since one end portion of each ring link member 11 is enlarged and the ring link members 11 are pivotally connected to one another through the pin members 15, a complicated fabrication process is required, and a pin connection step of the ring link members 11 is required, which is inconvenient and disadvantageous. Also, the heads of the pin members 15 radially project outwards and inwards, and the outer surfaces of the ring link members 11 and the pin connection portions thereof are not flat. Hence, there are fear and danger that the uneven surface of the bending tube part 6 will damage the inside wall of an internal organ of a body or the like. In the conventional bending tube part described above, the heads of the pin members 15 can contact the wires 17. In order to prevent this contact between the pin member and the wire, the wire guide members 16 are radially shifted inwards, which restricts the effective space within the ring link members 11.

SUMMARY OF THE INVENTION

It is therefore an object of the present invention to provide an endoscope having a bending tube part, free from the aforementioned defects and disadvantages of the prior art, which is capable of elongating the life of the bending tube part and positioning an end part of a flexible insertion tube to a proper position even after a part of the bending tube part is contacted with an inside wall of an object to be observed, and which has a simple structure and is fabricated in a simple manner.

It is another object of the present invention to provide a bending tube part, free from the aforementioned defects and disadvantages of the prior art, which is capable of elongating the life of the bending tube part and positioning an end part of a flexible insertion tube to a proper position even after a part of the bending tube part is contacted with an inside wall of an object to be observed, and which has a simple structure and is fabricated in a simple manner.

In accordance with one aspect of the present invention, there is provided an endoscope comprising an operating body having an operating knob thereon, a flexible insertion tube connected to the operating body, including a flexible tube part, a bending tube part and an end part in series, and wires for bending the bending tube part of the flexible insertion tube by operating the operating knob, the bending tube part comprising ring link members having a tubular form, and flexible connection members for coupling adjacent two ring link members at upper and lower or left and right sides thereof, alternately, to connect the ring link members with one another in series.

In accordance with another aspect of the present invention, there is provided a bending tube part comprising ring link members having a tubular form, and flexible connection members for coupling adjacent two ring link members at upper and lower or left and right sides thereof, alternately, to connect the ring link members with one another in series.

BRIEF DESCRIPTION OF THE DRAWINGS

The present invention will be more apparent from the following description of the preferred embodiments thereof in connection with the accompanying drawings, in which.

DESCRIPTION OF THE PREFERRED EMBODIMENTS

Figure 1:
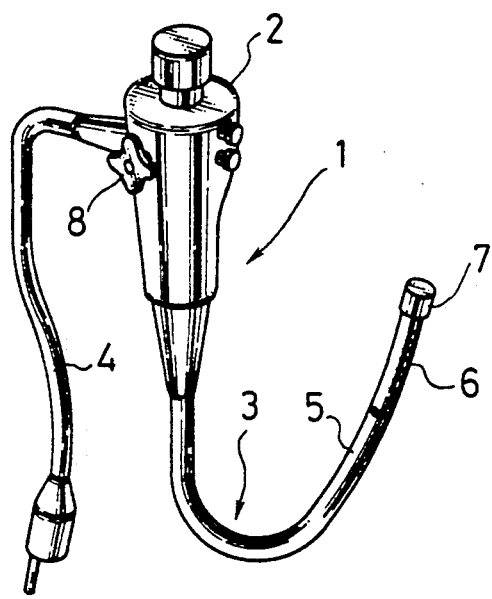
FIG. 1 is a perspective view of an endoscope including a bending tube part.
Figure 2:
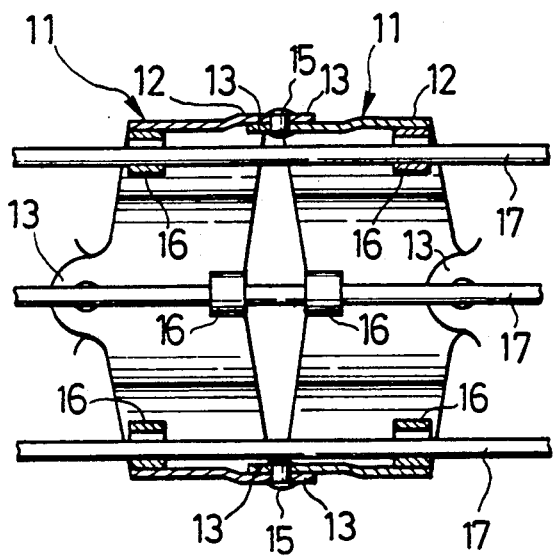
FIG. 2 is a fragmentary cross sectional view of a conventional bending tube part of an endoscope.
Figure 3A:
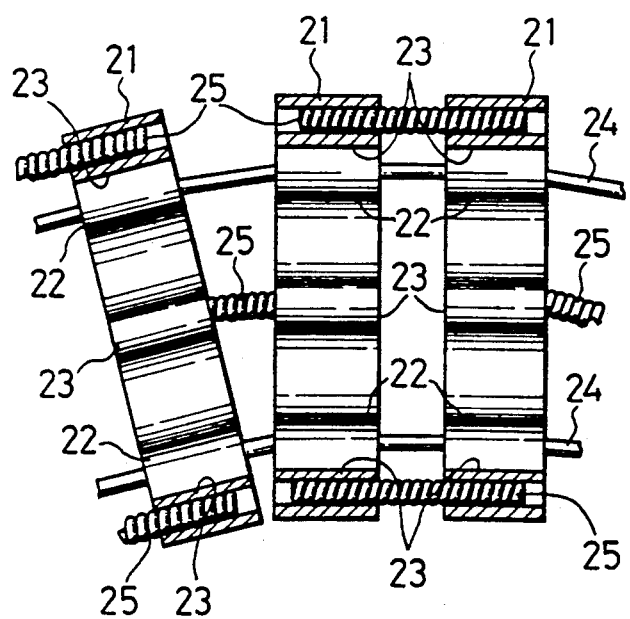
FIG. 3 is a cross sectional view of a first embodiment of a bending tube part of an endoscope according to the present invention.
Figure 3B:
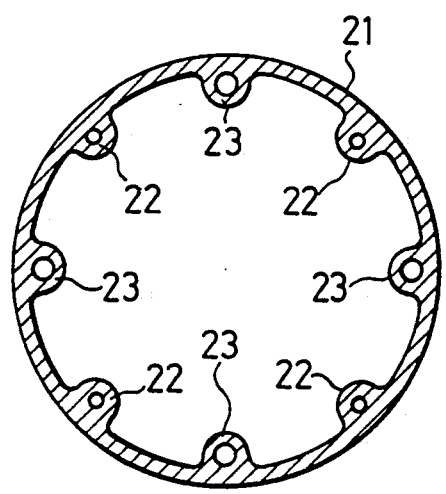

Referring now to the drawings, there is shown in FIG. 3 the first embodiment of a bending tube part 6 of an endoscope 1 according to the present invention, which comprises an operating body 2, a flexible insertion tube 3 and an electric cord 4 to be connection to an electrical plug, the flexible insertion tube 3 including a flexible tube part 5, the bending tube part 6 connected to the end of the flexible tube part 5, and an end part 7 connected to the end of the bending tube part 6, as shown in FIG. 1. The bending tube part comprises a plurality of ring link members 21 having a tubular form, connected with one another in series through flexible connection members 25. In the ring link members 21, a light guide, electric leads for an image guide, the CCD and the like, tubes for feeding air and water and sucking air, a forceps channel and the like are passed. Usually, the ring link members 21 are covered by a braid and an outer cover.

Each ring link member 21 is integrally provided with four wire guide members 22 having a tubular form and four connection member retainers 23 having a tubular form on the inside wall by a wire-cut electric discharge machining or a press punch machining. These four wire guide members 22 and four connection member retainers 23 are alternately aligned at equal intervals. The four wire guide members 22 are aligned at an angle of 90 degrees around the axis of the ring link member 21, and the four connection member retainers 23 are also aligned at an angle of 90 degrees around the axis of the ring link member 21. Operating wires 24 for conducting the bending operation of the bending tube part 6 are passed through the wire guide members 22. One end of each of the wires 24 is secured to the ring link member 21 positioned in the front end and the other ends of the wires 24 are connected to the knob 8 of the body 2. Both end portions of flexible connection members 25 having a slender or elongate form are fitted in the holes of the every other connection member retainers 23 of the two adjacent ring link members 21, and may be secured therein by deposition such as soldering and brazing or adhesion, as occasion demands, to connect the two adjacent ring link members 21 at a certain distance away from one to another. That is, as shown in FIG. 3a, in this embodiment, two adjacent ring link members 21 are connected with one another by two connection members 25 at the upper and lower or left and right connection member retainers 23, alternately.

As to each elongate connection member 25, it is flexible in the transverse direction, i.e., the direction approximately perpendicular to its longitudinal direction when a bending stress is given to the connection member 25, but is not deformed in the longitudinal direction even when a compression stress is given to it. The connection member 25 preferably comprises a metal coil such as a tension coil or a tight coil, a metal coil spring, a metal wire, a metal tube or a metal stick or rod, and materials shown in Table 1 can be preferably used for producing these members.

TABLE 1

| material | | G: kgf/mm² (N/mm²) |
| --- | --- | --- |
| Spring steel material | | $8 \times 10^3$ $(78 \times 10^3)$ |
| Hard steel wire | | $8 \times 10^3$ $(78 \times 10^3)$ |
| Piano wire | | $8 \times 10^3$ $(78 \times 10^3)$ |
| Oil-tempered wire | | $8 \times 10^3$ $(78 \times 10^3)$ |
| Stainless steel wire | AISI 302 AISI 304 AISI 316 | $7 \times 10^3$ $(69 \times 10^3)$ |
| | AISI 631 J1 | $7.5 \times 10^3$ $(74 \times 10^3)$ |
| Brass wire | | $4 \times 10^3$ $(39 \times 10^3)$ |
| Nickel silver wire | | $4 \times 10^3$ $(39 \times 10^3)$ |
| Phosphor bronze wire | | $4.3 \times 10^3$ $(42 \times 10^3)$ |
| Beryllium copper wire | | $4.5 \times 10^3$ $(44 \times 10^3)$ |

G: Modulus of transverse elasticity (As G decreases, flexibility increases)

A synthetic resin coil or coil spring, a synthetic resin tube such as a silicon resin tube, a synthetic resin stick or rod such as a hard rubber stick or rod, or the like can also be used as the connection member 25. In order to improve the sliding property, the ring link members 21 including the wire guide members 22 and the connection member retainers 23 and the connection members 25 may be made of a solid lubricity material such as molybdenum disulfide, or may be coated by a solid lubricity material such as molybdenum disulfide or synthetic resin such as Teflon (trade name) (polytetrafluoroethylene).

In this embodiment, as shown in FIG. 3a, when a bending stress is given to the ring link members 21, for instance, by pulling and slackening the wires 24 by operating the knob 8, the connection members 25 coupling the two adjacent ring link members 21 are bent, but the connection members 25 are substantially not deformed in the longitudinal direction even when a compression stress is imparted to the connection members 25. That is, when the bending tube part 6 is not bent, the distance between the two ring link members 21 is always kept to the fixed value. In turn, when the bending tube part 6 is bent, only the connection members 25 receiving the bending stress are bent while the other connection members 25 receiving no bending stress are substantially not bent. Hence, the bending tube part 6 can realize the desired bending operation.

As described above, according to the first embodiment of the present invention, since there is no contact pivot movement between the link members and pivot pins in the conventional bending tube part, no friction is caused, and thus the life of the bending tube part 6 can be prolonged. Further, since the connection members 25 are arranged within the outer surfaces of the ring link members without any trouble, there is no projection from the outer surfaces of the ring link members, and hence the bending tube part 6 together with the end part 7 of the flexible insertion tube 3 can be smoothly inserted into an object to be observed.

Although the four wire guide members 22 are aligned at angles of 90 degrees around the axis of the ring link member 21 and the four connection member retainers 23 are similarly aligned at angles of 90 degrees around the axis of the ring link member 21 in the above described embodiment, however, of course, the numbers of the connection member retainers and wire guide members of the ring link member can be separately determined to be other suitable values, and the angles of the adjacent two connection member retainers or wire guide members of the ring link member around the axis thereof can be independently determined to be other proper values, with the same effects and advantages as obtained in the first embodiment. Further, although the bending tube part applied to the flexible insertion tube of the endoscope has been described in the above embodiment, however, this bending tube part can also be applied to other various devices or members such as manipulators and so forth.

Figure 4A:
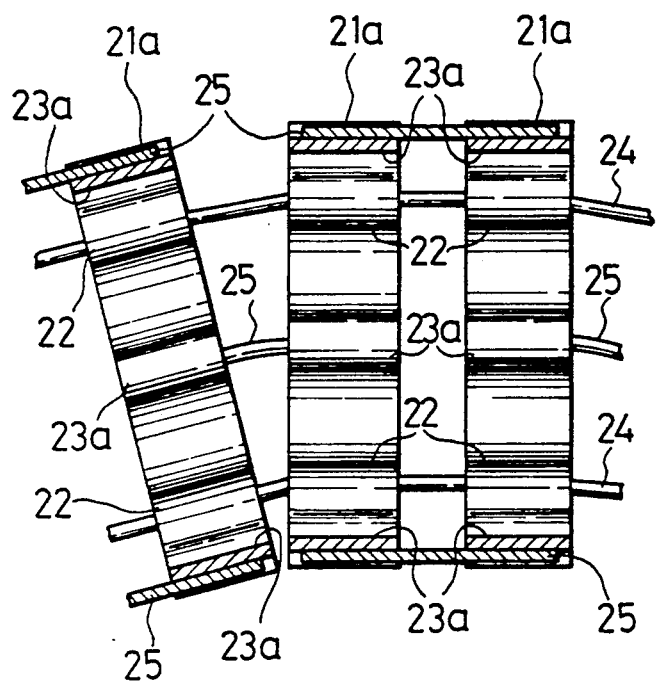
FIG. 4 is a cross sectional view of a second embodiment of a bending tube part of an endoscope according to the present invention.
Figure 4B:
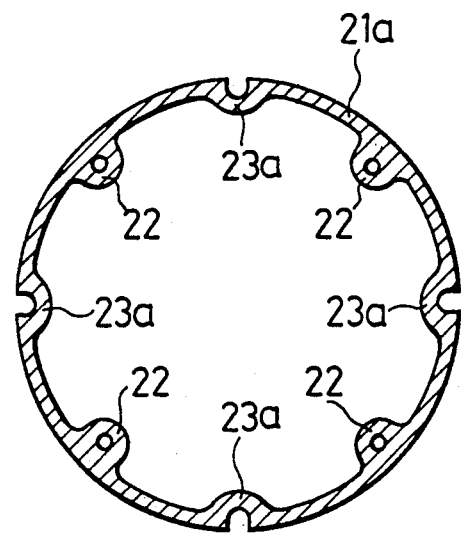

In FIG. 4, there is shown the second embodiment of the bending tube part 6 of the endoscope 1 according to the present invention, having the same construction as that of the first embodiment, except that each ring link member 21a is provided with four connection member retainer 23a in the similar manner to the first embodiment shown in FIG. 3, and each connection member retainer 23a includes a groove at the outer surface of the ring link member 21a instead of the hole of the connection member retainer 23 of the first embodiment. In this embodiment, a metal wire or rod to be inserted into the groove of the connection member retainer 23a is conveniently used as the connection member 25. In this case, the grooves of the connection member retainers 23a can be readily formed. Further, the connection member retainers 23a project inwards at a distance less than that of the first embodiment, and hence the inside available space can be widened.

Figure 5A:
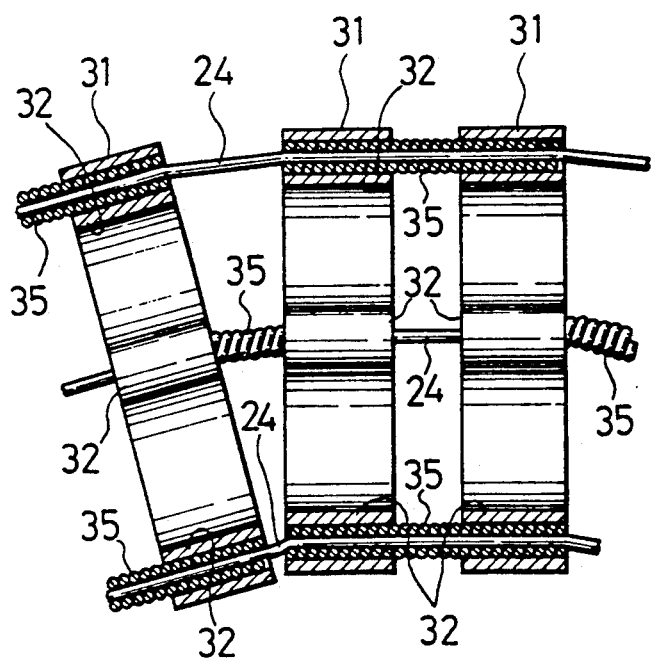
FIG. 5 is a cross sectional view of a third embodiment of a bending tube part of an endoscope according to the present invention.
Figure 5B:
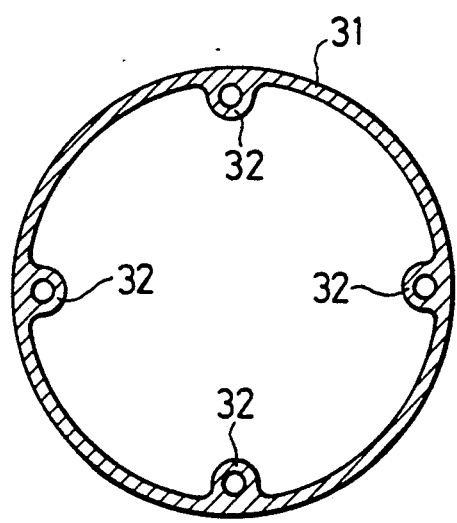

In FIG. 5, there is shown the third embodiment of the bending tube part 6 of the endoscope 1 according to the present invention. In this embodiment, each ring link member 31 is formed with only four connection member retainers 32 in the same manner as the first embodiment, but no wire guide members. Tubular connection members 35 are inserted into the holes of the connection member retainers 32 of the two adjacent ring link members 31 in the same manner as the first embodiment, and operating wires 24 are passed through the holes of the connection members 35. In this case, the same effects and advantages as those of the first embodiment can be obtained. Further, since no wire guide member is provided, the inside space of the ring link members 31 can be more effectively utilized.

Figure 6A:
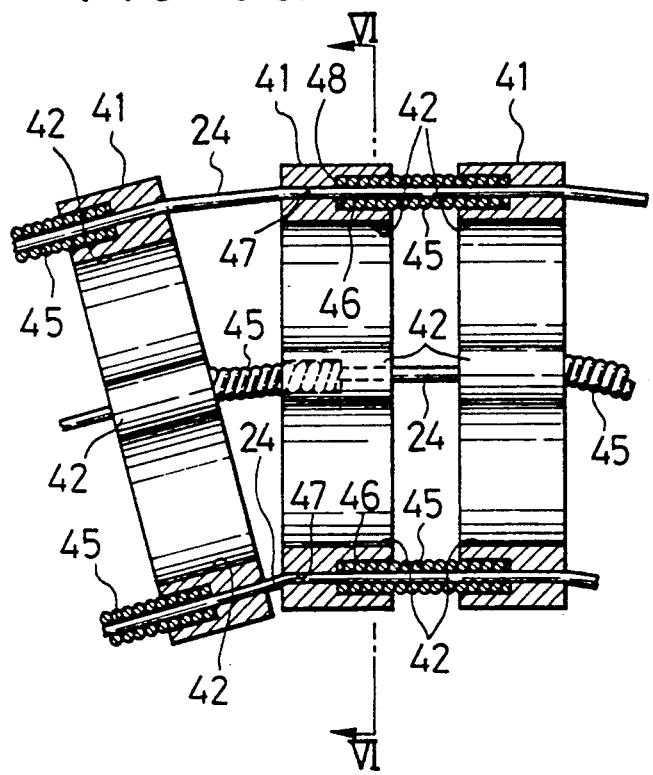
FIG. 6 is a cross sectional view of a fourth embodiment of a bending tube part of an endoscope according to the present invention.
Figure 6B:
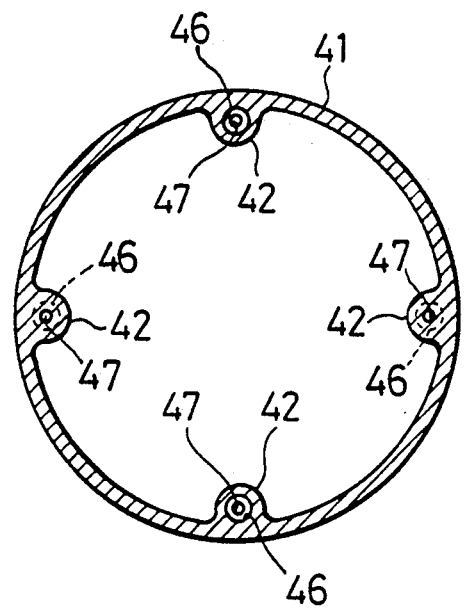

In FIG. 6, there is shown the fourth embodiment of the bending tube part 6 of the endoscope 1 according to the present invention. FIG. 6b is a vertical cross sectional view, taken along the line VI—VI in FIG. 6a. In this embodiment, each ring link member 41 is provided with four connection member retainers 42 in the same manner as the third embodiment shown in FIG. 5. However, each connection member retainer 42 is formed with a double diameter hole, i.e., an outer hole 46 and an inner hole 47 along an axis thereof, the diameter of the outer hole 46 is larger than that of the inner hole 47, and a stopper portion 48 between the outer and inner holes 46 and 47. As shown in FIG. 6, the outer holes 46 of the upper and lower connection member retainers 42 are positioned in the opposite end of the ring link member 41 to the outer holes 46 of the left and right connection member retainers 42. Connection members 45 having a somewhat short length are fitted into the outer holes 46 of the connection member retainers 42 of the two adjacent ring link members 41, and operating wires 24 are passed through not only the inner holes 47 of the connection member retainers 42 but also the holes of the connection members 45.

In this case, the same effects and advantages as those obtained in the third embodiment can be resulted. Further, in this embodiment, the connection members 45 inserted into the outer holes 46 of the connection member retainers 42 are stopped by the stopper portions 48 thereof, and the deposition or adhesion step of the connection members 45 in the outer holes 46 of the connection member retainers 42 is unnecessary when the bending tube part 6 is assembled. Also, the connection members 45 will not fall off of the connection member retainers 42 of the ring link members 41 during operation of the endoscope, with the result of stable and reliable bending operation of the bending tube part 6.

Figure 7:
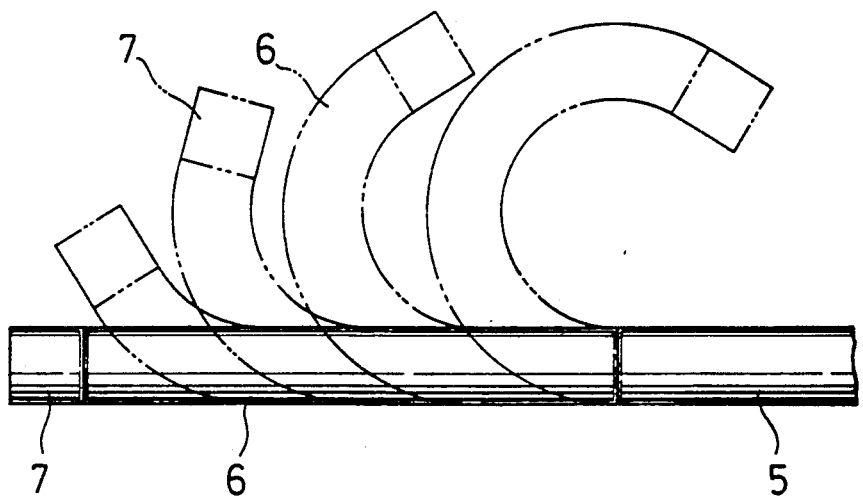
FIG. 7 is a schematic view showing bending shapes of a bending tube part of an endoscope according to the present invention.

In the first to fourth embodiments described above, the flexibility of the connection members 25, 35 and 45 may be varied. For example, the flexibility of the connection members is gradually reduced from the front end portion (near the end part 7) of the bending tube part 6 to the rear end portion (near the flexible tube part 5). In this case, when the bending tube part 6 is bent by pulling the wires 24, the bending tube part 6 is successively bent from the front end portion (near the end part 7) to the rear end portion (near the flexible tube part 5), as shown in FIG. 7. This flexibility variation of the connection members can be performed, for instance, by using the different materials tabulated in Table 1, or by changing the diameter of the wires using the same material. In the latter case, a finer wire has a larger flexibility, and thus the finer wire is used in the front end portion while a thicker wire is used in the rear end portion. In this case, as described above, the operation area of the bending tube part 6 can be minimized, and the narrow space can be effectively observed without any trouble. Further, the positioning of the end part 7 of the flexible insertion tube 3 can be exactly, properly and quickly carried out even when the part of the bending tube part 6 is contacted with the wall of the object to be observed.

Although the present invention has been described in its preferred embodiments thereof with reference to the accompanying drawings, it is readily understood that the present invention is not restricted to the preferred embodiments and that various changes and modification can be made in the present invention by a person skilled in the art without departing from the spirit and scope of the present invention.

What is claimed is:

1. An endoscope comprising:
an operating body having an operating knob thereon;
a flexible insertion tube connected to the operating body, including a flexible tube part, a bending tube part and an end part, in series; and
wires for bending the bending tube part of the flexible insertion tube by operating the operating knob,
the bending tube part comprising:
ring link members having peripheral holes, the wires passing through the peripheral holes; and
flexible connection members for coupling two adjacent ring link members at alternate pairs of sides to connect the ring link members with one another in series, each connection member being composed of a single flexible elongate member which is flexible in a direction approximately perpendicular to its longitudinal direction, the opposite ends of each flexible connection member being secured to the ring link members.

2. The endoscope of claim 1, wherein each link ring member includes four peripheral holes at four sides, and each flexible connection member has a tubular form and includes a through-hole, and wherein each flexible connection member is secured at the peripheral holes of the two adjacent ring link members, and the wires pass through the holes of the flexible tubular connection members.

3. The endoscope of claim 2, wherein each peripheral hole is a double diameter hole composed of a larger hole and a smaller hole connected thereto, and wherein each flexible tubular connection member having the through-hole is secured in the larger hole, and the wires pass through both the small holes and the through-holes of the flexible tubular connection members.

4. The endoscope of claim 1, wherein each ring link member also includes four peripheral retainers at four sides, separate from the peripheral holes of each ring link member, and the flexible connection members are secured to the ring link members at the four peripheral retainers.

5. The endoscope of claim 4, wherein each peripheral retainer includes a hole therein in which the flexible connection member is secured.

6. The endoscope of claim 4, wherein each peripheral retainer includes a groove therein in which the flexible connection member is secured.

7. The endoscope of claim 1, wherein each ring link member includes peripheral wire guide members each having a hole through which the wire passes.

8. The endoscope of claim 1, wherein the flexibility of the flexible connection members is gradually reduced from the front end portion to the rear end portion of the bending tube part.

9. The endoscope of claim 1, wherein the flexible connection members are flexible in the transverse direction to their longitudinal axes when a bending stress is applied thereto, but are not deformed in the longitudinal direction thereof when a compression stress is applied to the flexible connection members.

10. The endoscope of claim 2, wherein the flexible connection member comprises a metal coil.

11. A bending tube part comprising:
ring link members having peripheral holes, the wires passing through the peripheral holes; and
flexible connection members for coupling two adjacent ring link members at alternate pairs of sides to connect the ring link members with one another in series, each flexible connection member being composed of a single flexible elongate member which is flexible in a direction approximately perpendicular to a longitudinal direction thereof, opposite ends of each flexible connection member being secured to the ring link members.

12. The endoscope of claim 11, wherein each link ring member includes four peripheral holes at four sides, each flexible connection member having a tubular form includes a through-hole, and wherein each flexible connection member is secured at the peripheral holes of the two adjacent ring link members, and the wires pass through the holes of the flexible tubular connection members.

13. The endoscope of claim 12, wherein each peripheral hole is a double diameter hole composed of a larger hole and a smaller hole centered therein, and wherein each flexible tubular connection member having the through-hole is secured in the larger hole, and the wires pass through the small holes and also through the through-holes of the flexible tubular connection members.

14. The bending tube part of claim 11, wherein each ring link member also includes four peripheral retainers at four sides, separate from the peripheral holes of each ring link member, and the flexible connection members are secured to the ring link members at the four peripheral retainers.

15. The endoscope of claim 14, wherein each peripheral retainer includes a hole therein in which the flexible connection member is secured.

16. The endoscope of claim 14, wherein each peripheral retainer includes a groove therein in which the flexible connection member is secured.

17. The endoscope of claim 11, wherein each ring link member includes peripheral wire guide members, each having a hole through which the wire passes.

18. The endoscope of claim 11, wherein the flexibility of the flexible connection member is gradually reduced from the front end portion to the rear end portion of the bending tube part.

19. The endoscope of claim 11, wherein the flexible connection members are flexible in the transverse direction thereof when a bending stress is applied to the flexible connection members, but are not deformed in the longitudinal direction thereof when a compression stress is given to the flexible connection members.

* * * * *